(12) United States Patent
Weber (10) Patent No.: US 9,084,627 B2
(45) Date of Patent: Jul. 21, 2015

(54) ATHERECTOMY POSITIONING DEVICE

(71) Applicant: Boston Scientific Scimed, Inc., Maple Grove, MN (US)

(72) Inventor: Jan Weber, Maastricht (NL)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 280 days.

(21) Appl. No.: 13/653,723

(22) Filed: Oct. 17, 2012

(65) Prior Publication Data

US 2013/0096588 A1   Apr. 18, 2013

Related U.S. Application Data

(60) Provisional application No. 61/548,412, filed on Oct. 18, 2011.

(51) Int. Cl.
| | |
|---|---|
| A61B 17/22 | (2006.01) |
| A61B 17/3207 | (2006.01) |
| A61B 17/00 | (2006.01) |
| A61B 17/32 | (2006.01) |
| A61B 19/00 | (2006.01) |

(52) U.S. Cl.
CPC ... *A61B 17/320725* (2013.01); *A61B 17/32075* (2013.01); *A61B 17/320758* (2013.01); *A61B 2017/00292* (2013.01); *A61B 2017/22038* (2013.01); *A61B 2017/22049* (2013.01); *A61B 2017/22098* (2013.01); *A61B 2017/320004* (2013.01); *A61B 2017/320052* (2013.01); *A61B 2019/306* (2013.01)

(58) Field of Classification Search
CPC ........... A61B 17/22; A61B 17/320758; A61B 2017/003

USPC .......... 606/159, 167, 192; 604/96.01, 103.02, 604/264

See application file for complete search history.

(56) References Cited

U.S. PATENT DOCUMENTS

| | | | |
|---|---|---|---|
| 7,731,731 | B2 | 6/2010 | Abela |
| 7,854,755 | B2 | 12/2010 | Lafontaine et al. |
| 2006/0173475 | A1 | 8/2006 | Lafontaine et al. |

(Continued)

FOREIGN PATENT DOCUMENTS

| | | |
|---|---|---|
| EP | 0832608 A2 | 4/1998 |
| WO | 9423787 A1 | 10/1994 |

(Continued)

*Primary Examiner* — Victor Nguyen
(74) *Attorney, Agent, or Firm* — Seager, Tufte & Wickhem, LLC (57) ABSTRACT

Techniques are described for treating an occlusion in a patient. In one example, a system includes an atherectomy device configured to remove an occlusion from a body lumen and a positioning device that positions the atherectomy device adjacent to the occlusion. The positioning device includes a tubular body having first and second ends and defining a lumen therebetween, at least two fins engaged to the tubular body, wherein in a deployed state, the fins extend radially outward from the tubular body, and wherein in an undeployed state, the at least two fins wrap about one another and about the tubular body, a guide wire extending through the lumen, and first and second stopper members, each of the first and second stopper members engaged to the guide wire, wherein the first stopper member and the second stopper member substantially prevent movement of the tubular body along the guide wire.

16 Claims, 9 Drawing Sheets

(56) References Cited

U.S. PATENT DOCUMENTS

2006/0287667 A1 12/2006 Abela
2008/0045986 A1* 2/2008 To et al. .................. 606/159

FOREIGN PATENT DOCUMENTS

| WO | 2005086692 A2 | 9/2005 |
|----|---------------|--------|
| WO | 2008002865 A2 | 1/2008 |

* cited by examiner

ATHERECTOMY POSITIONING DEVICE

CROSS REFERENCE TO RELATED APPLICATIONS

This application claims priority from U.S. Application No. 61/548,412, filed on Oct. 18, 2011, the entire contents of which is hereby incorporated by reference.

TECHNICAL FIELD

This disclosure relates to medical devices and, more particularly, to atherectomy devices.

BACKGROUND

Vascular diseases, such as atherosclerosis and the like, have become quite prevalent in the modern day. These diseases may manifest themselves in a number of ways, often requiring different forms or methods of treatment for curing the adverse effects of the diseases. Vascular diseases, for example, may take the form of deposits or growths in a patient's vasculature which may restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

One treatment method involves removal of the occluding material. Devices used for such treatment methods, sometimes referred to as atherectomy devices, use a variety of material removal means, such as rotating cutters or ablaters, for example, to remove the occluding material. The material removal device is typically rotated via a drive shaft that extends out of the vascular of the patient and to an electric motor.

In operation, an atherectomy device is typically advanced over a guide wire placed in-vivo until the material removal device is positioned just proximal to the occluded site. The motor is used to rotate the drive shaft and the material removal device, and the material removal device is moved through the occluded vessel. The material removal device removes the material from the vessel, rather than merely displacing or reforming the material as in a balloon angioplasty procedure.

SUMMARY

In general, this disclosure describes techniques for positioning an atherectomy device at the site of an occlusion. By accurately positioning the atherectomy device, occlusions that would otherwise be difficult to treat, e.g., at a valve, can be ablated.

In one example, the disclosure is directed to a method in which a system for treating an occlusion in a patient. The system comprises an atherectomy device configured to remove an occlusion from a body lumen and a positioning device that positions the atherectomy device adjacent to the occlusion. The positioning device comprises a tubular body having a first end and a second end and defining a lumen therebetween, at least two fins engaged to the tubular body, wherein in a deployed state, the at least two fins extend radially outward from the tubular body, and wherein in an undeployed state, the at least two fins wrap about one another and about the tubular body, a guide wire extending through the lumen, and first and second stopper members, each of the first and second stopper members engaged to the guide wire, wherein the first stopper member and the second stopper member substantially prevent movement of the tubular body along the guide wire.

In another example, the disclosure is directed to a positioning device that positions an atherectomy device adjacent to an occlusion in a patient. The positioning device comprises a tubular body having a first end and a second end and defining a lumen therebetween, at least two fins engaged to the tubular body, wherein in a deployed state, the at least two fins extend radially outward from the tubular body, and wherein in an undeployed state, the at least two fins wrap about one another and about the tubular body, a guide wire extending through the lumen, and first and second stopper members, each of the first and second stopper members engaged to the guide wire, wherein the first stopper member and the second stopper member substantially prevent movement of the tubular body along the guide wire.

In another example, this disclosure is directed to a method for positioning an atherectomy device adjacent to an occlusion in a patient. The method comprises delivering, over a guide wire, a positioning device through a valve and into a chamber of the heart, wherein the positioning device comprises a tubular body having a first end and a second end and defining a lumen therebetween, a plurality of fins engaged to the tubular body, wherein in a deployed state, the plurality of fins extending radially outward from the tubular body, and, in an undeployed state, the plurality of fins wrap about one another and about the tubular body, a guide wire extending through the lumen, and first and second stopper members, each of the first and second stopper members engaged to the guide wire, wherein the first stopper member and the second stopper member substantially prevent movement of the at least two fins along the guide wire. The method further comprises removing a guide catheter that is disposed about at least a portion of the positioning device and allowing the plurality of fins to extend radially outward from the tubular body, pulling the positioning device proximally through the valve such that a portion of the positioning device is positioned within the chamber of the heart and another portion of the positioning device is positioned within an artery, whereby the extended fins define a plurality of sections within the artery, guiding an atherectomy device into one of the plurality of sections defined by the fins and adjacent the occlusion, and removing the occlusion.

The details of one or more aspects of the disclosure are set forth in the accompanying drawings and the description below. Other features, objects, and advantages will be apparent from the description and drawings, and from the claims.

DETAILED DESCRIPTION

Calcification of native and artificial aortic heart valves, for example, restricts the opening of the valve, thereby leading to decreased cardiac output. Currently, replacement of the calcified valve is the only viable option. During an aortic valve replacement procedure, for example, the old, calcified aortic valve leaflets are pushed aside and compressed against the wall of aorta by the replacement valve. In some instances, however, it may be desirable to treat the calcified valve leaflets rather than replace them.

As indicated above, atherectomy devices use a variety of material removal means, such as rotating cutters or ablaters, for example, to remove occluding material, e.g., calcified material. For example, the Rotablator®, a commercially available rotational atherectomy device from Boston Scientific Corporation, may be used to treat calcified material. Using currently available techniques, however, it is difficult to position an atherectomy device with sufficient accuracy to treat calcified areas of the valve, e.g., the base of the valve.

In accordance with this disclosure, techniques are described for positioning an atherectomy device at the site of an occlusion, e.g., a calcified valve. By accurately positioning the atherectomy device, occlusions, e.g., calcifications, that would otherwise be difficult to treat, e.g., at a valve, can be ablated by an atherectomy device. As described in more detail below and in accordance with this disclosure, a clinician may insert a finned positioning device into the opening in between the valve leaflets, thereby dividing the vessel or artery, e.g., aorta, into sections. The clinician may then guide an atherectomy device, e.g., as shown and described below with respect to FIG. 1, into one of the sections created by the finned positioning device toward a calcified area, e.g., at the base of the valve.

In addition, using the techniques described in this disclosure, occlusions that are positioned against a wall of an artery, e.g., the aortic arch, may be removed. For example, an atherectomy device may be difficult to accurately place within the aorta because the aorta is relatively large in size in comparison with the atherectomy device. However, by using the positioning device of this disclosure to divide the aorta, for example, into multiple smaller sections helps a clinician to accurately position the atherectomy device near the occlusion, e.g., calcification, that would otherwise be difficult to treat.

Furthermore, the techniques described in this disclosure allow an occlusion in one section created by the positioning device to be treated by the atherectomy device while the inlet to the carotid artery is positioned in another section. In this manner, the positioning device described below helps to prevent debris created by the atherectomy device from being flushed through the carotid artery towards the brain. All debris removed by the atherectomy device that is not captured in by its own filter is flushed downward in the body and not up to the brain. In one example, to test whether the artherectomy device is in the same section as the inlet of the carotid artery, a clinician may inject a contrast media via the atherectomy device and see where the contrast fluid ends up before beginning the atherectomy procedure.

Using the techniques of this disclosure, the calcified leaflets may be treated prior to replacement. For example, in some cases, bulky calcifications on valve leaflets prevent optimal placing of a new valve. By using the positioning device described below, calcifications may be cut and removed using the blades of the positioning device (FIG. 9) and an atherectomy device, and then a new valve may be positioned. In some cases, removing the calcification on the old valve prior to replacement may reduce the need to use a valvoplasty balloon during the procedure.

Figure 1:
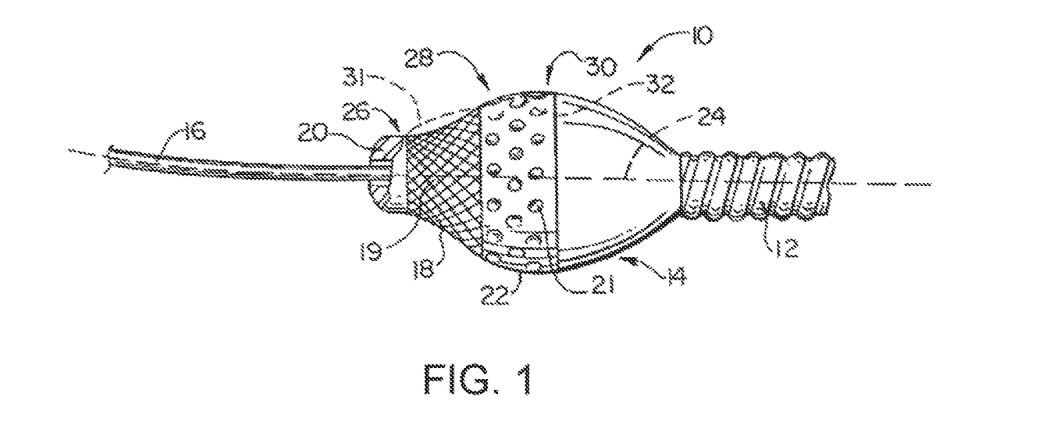
FIG. 1 is a side elevational view of an example atherectomy device that may be used along with the positioning device of this disclosure to ablate occlusions in a body lumen.

FIG. 1 is a side elevational view of an example atherectomy device that may be used along with the positioning device of this disclosure, which is described in more detail below, to ablate occlusions in a body lumen. The atherectomy device is generally shown at 10, and includes a flexible drive shaft 12 and an ablation burr 14. The flexible drive shaft 12 and ablation burr 14 have a lumen extending therethrough to receive a guide wire 16, as shown.

In operation, the guide wire 16 is percutaneously inserted through the vasculature and past the desired occlusion site. The atherectomy device 10 is then slid over the guide wire 16 until the ablation burr 14 is positioned just proximal to the occlusion site. A guide catheter may be used to assist in the positioning of both the guide wire 16 and the atherectomy device 10. The proximal end of the drive shaft remains outside the body and is attached to an electric motor. The motor rotates the atherectomy device while the atherectomy device is advanced distally through the occlusion site. The ablation burr 14 removes the occluding material by ablation.

In one example configuration, the atherectomy device 10 comprises a flexible drive shaft 12 attached to an ablation burr 14, where the flexible drive shaft 12 and the ablation burr 14 are disposed about a central axis 24. The ablation burr 14 has a first cross section 26 spaced from a second cross section 28, where the second cross section 28 has a larger cross sectional area than the first cross section 26. The ablation burr 14 further has a first outer surface 18 that extends between the first cross section 26 and the second cross section 28, and extends inward toward the central axis 24 relative to an imaginary line 31 that extends between the first cross section 26 and the second cross section 28 as shown.

The atherectomy device 10 may further have a third cross section 30 spaced relative to the second cross section 28, where the ablation burr 14 includes a second outer surface 22 that extends between the second cross section 28 and the third cross section 30. The second outer surface 22 extends outward away from the central axis 24 relative to an imaginary line 32 that extends between the second cross section 28 and the third cross section 30.

In some configurations, the ablation burr 14 is generally elliptical in shape, except for a concave shaped leading surface 18 as shown. An abrasive grit 19, shown in a cross hatch, is disposed on the concave shaped leading surface 18. The abrasive grit may be diamond grit. Extending distally from the concave shaped leading surface 18 is a distal tip portion 20, and extending proximally from the concave shaped leading surface 18 is a convex shaped portion 22. Both the distal tip portion 20 and the convex shaped portion 22 preferably have non-abrasive surfaces. In this configuration, the abrasive grit 19 is effectively prevented from engaging a vessel wall regardless of the orientation of the ablation burr 14 within a vessel.

It is difficult to position an atherectomy device such as atherectomy device 10 of FIG. 1 with sufficient accuracy to treat calcified areas of the valve, e.g., the base of a valve, for example. As described in detail below, a practitioner may insert a finned positioning device into the opening in between the valve leaflets, thereby dividing the vessel or artery, e.g., aorta, into sections. The practitioner may then guide an atherectomy device, e.g., atherectomy device 10 of FIG. 1, into one of the sections created by the finned positioning device toward a calcified area, e.g., at the base of the valve.

Figure 2:
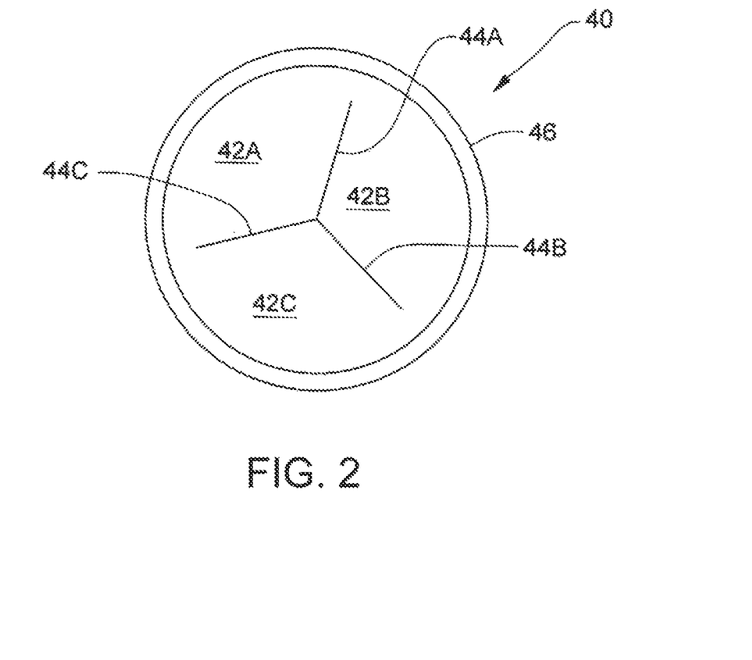
FIG. 2 is an end view of a heart valve.

FIG. 2 is a top view of a heart valve. The heart valve depicted in FIG. 2, shown generally at 40, is a tricuspid valve, e.g., an aortic valve. Heart valve 40 includes leaflets 42A, 42B, and 42C (collectively referred to herein as "leaflets 42"). Each leaflet is separated by openings 44A, 44B, 44C (collectively referred to herein as "openings 44"). Leaflets 42 of heart valve 40 are supported by a fibrous ring known as a valve annulus or base 46.

A degenerative process affecting heart valves, e.g., aortic valves, involves the calcification of fibrous base 46 (not shown in FIG. 2). Calcification of base 46 is caused by the accumulation of calcium deposits along and beneath base 46. As indicated above, although atherectomy devices may be used to treat calcified material, it is difficult to position the atherectomy device with sufficient accuracy to treat calcified areas of the valve, e.g., the base of the valve.

Figures 3, 4, 5:
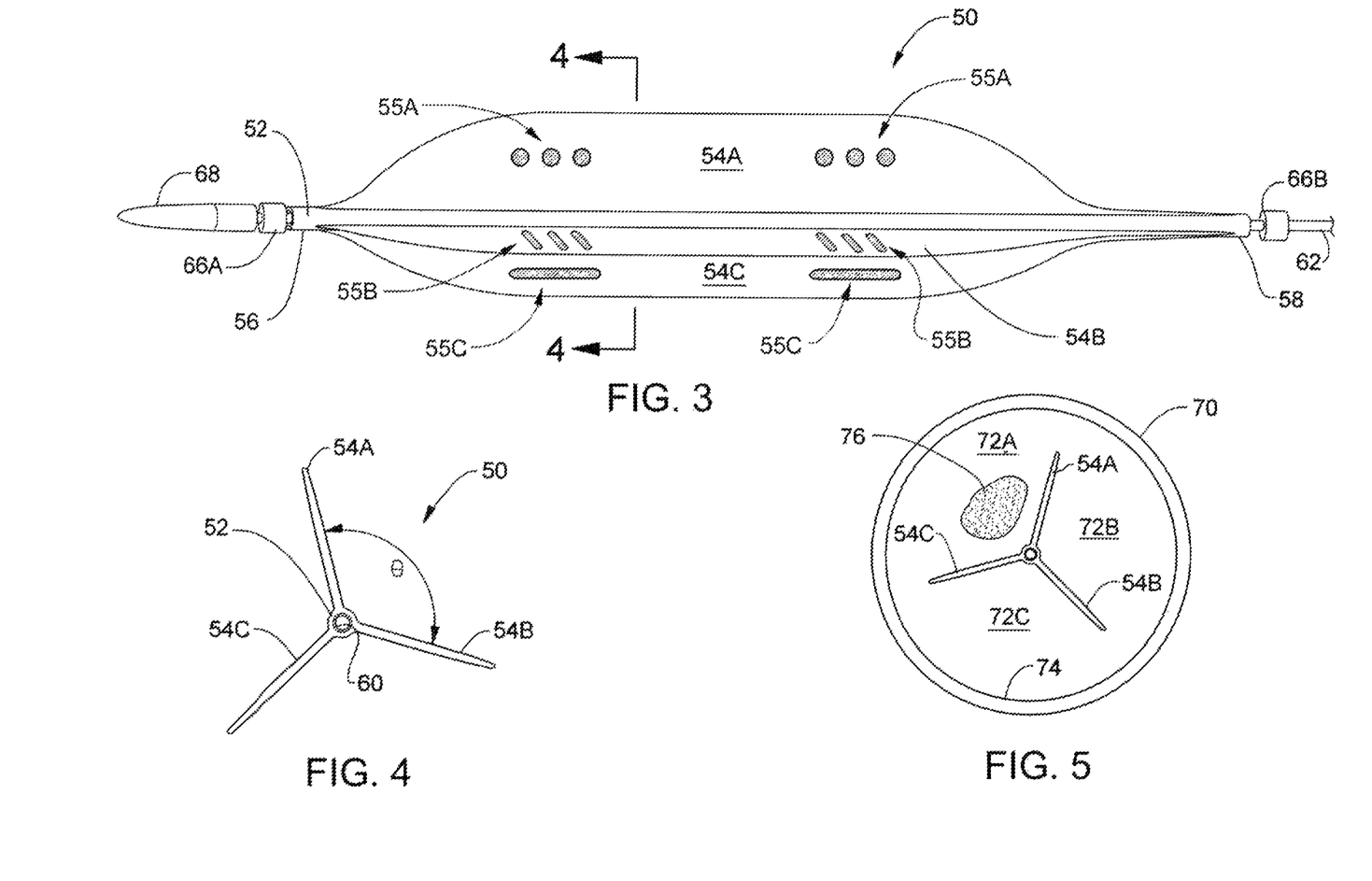
FIG. 3 is a side view of one example of a positioning device in an unwrapped state, in accordance with this disclosure.
FIG. 4 is an end cross-sectional view of the example positioning device of FIG. 3.
FIG. 5 is an end view of the positioning device shown in FIG. 4 positioned adjacent an occlusion within a body lumen, in accordance with this disclosure.

FIG. 3 is a side view of one example of a positioning device that may be used to position an atherectomy device (e.g., a Rotablator® atherectomy device, athrectomy device 10 of FIG. 1, and the like) adjacent to an occlusion, e.g., calcification, within a patient. The positioning device, shown generally at 50 in an unwrapped or deployed state, includes tubular body 52 and a plurality of fins, e.g., fins 54A, 54B, and 54C (collectively referred to in this disclosure as "fins 54") engaged to the tubular body.

In one example configuration, fins 54 are made from a soft and resilient material, e.g., rubber, silicone rubber, polyurethane, and the like. A conventional extrusion process, for example, can be used to create a unitary structure comprising fins 54 and tubular body 52. Other construction techniques may also be used. For example, a plurality of fins may be formed and adhered to tubular body 52 via an adhesive material.

In some example configurations, fins 54 are dimensioned such that they can fit through the tri-shape opening of an aortic valve. In such configurations, each of fins 54 are relatively thin to allow positioning device 50 to be aligned and then pulled proximally through the opening defined by the valve leaflets of the valve.

As shown in FIG. 3, fins 54 extend radially outward from tubular body 52 in a deployed state. The resilient properties of the fin material, e.g., rubber, silicone rubber, polyurethane, and the like, allow fins 54 to unfold from a folded or undeployed state and return to their original, deployed shape without assistance.

As described in more detail below, when deployed, positioning device 50 and, in particular, fins 54 divide a body lumen of a patient, e.g., a vessel or artery, into multiple sections. The sections defined by the fins of positioning device 50 allow a clinician to accurately locate the atherectomy device against an occlusion, e.g., a calcification at the base of a heart valve. An end cross-sectional view of positioning device 50 in a deployed state and the sections created within the body lumen is shown and described in more detail below with respect to FIG. 4.

Tubular body 52 has first end 56 and second end 58 and defines lumen 60 (shown in FIG. 7) extending between first end 56 and second end 58. In some examples, positioning device 50 further includes guide wire 62, which extends through lumen 60 of tubular body 52. Tubular body 52 is configured to rotate about guide wire 62.

Figures 12, 13:
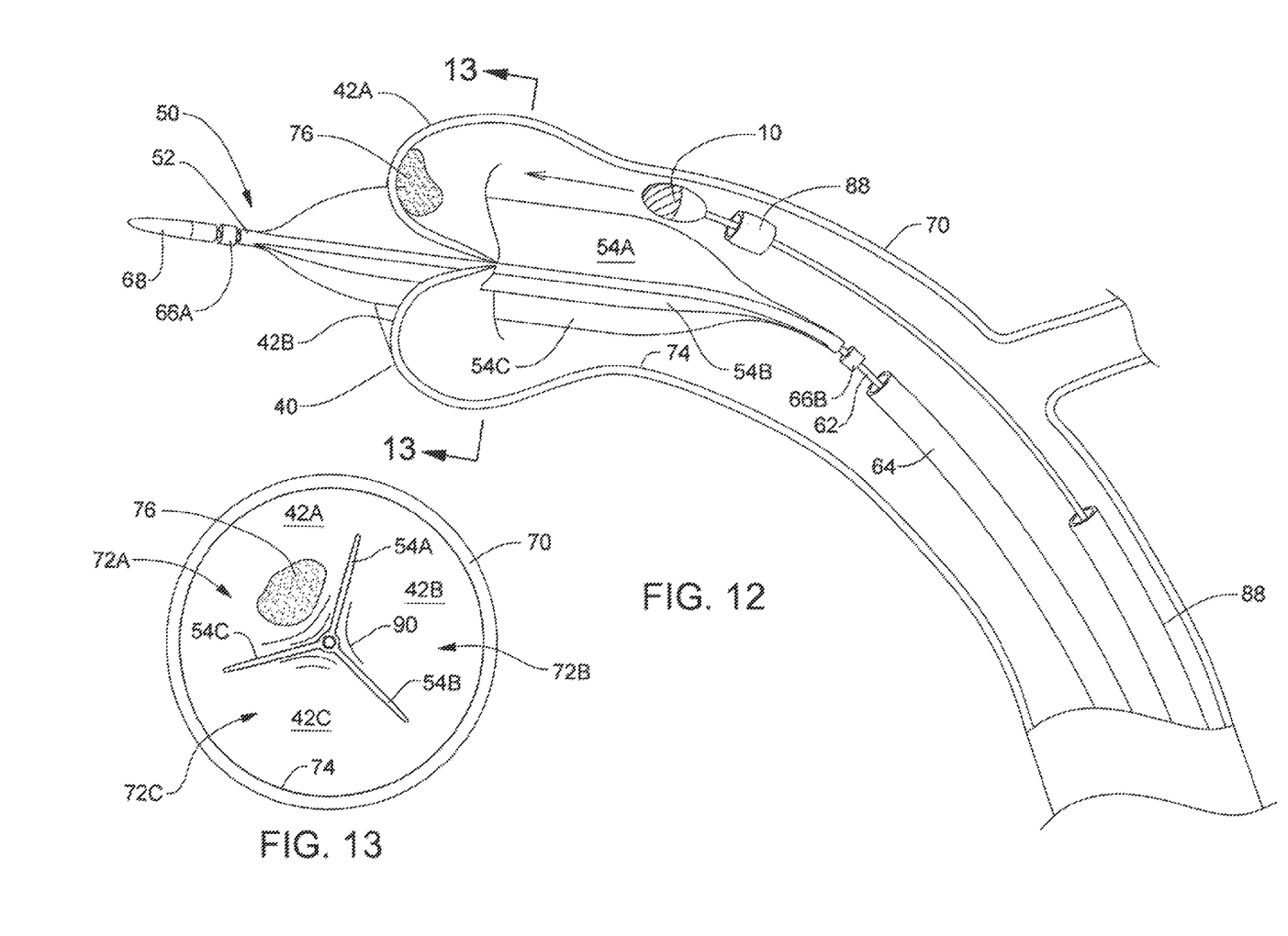
FIG. 12 is a side view of the example positioning device of FIG. 3 in an unwrapped state extending through an occluded heart valve, in accordance with this disclosure.
FIG. 13 is an end view of the occluded heart valve and positioning device shown in FIG. 12, in accordance with this disclosure.

In one example, positioning device 50 further includes guide catheter 64, shown in FIG. 12 in a retracted state, to allow positioning device 50 to be delivered in a wrapped state to the site of the occlusion. Guide catheter 64 has an interior surface defining a lumen with a diameter large enough to cover tubular body 52 and fins 54 when fins 54 are wrapped around each one another and tubular body 52 in a wrapped or undeployed state (shown below in FIG. 7).

Positioning device 50 further includes first stopper member 66A and second stopper member 66B (collectively referred to in this disclosure as "stopper members 66"). In one example configuration, first and second stopper members 66A, 66B are rings, e.g., ring shaped bushings. Each of stopper members 66 are engaged to guide wire 62 such that stopper members 66 substantially prevent longitudinal movement of tubular body 52 and fins 54 along guide wire 62. For example, in configuration, first stopper member 66A abuts first end 56 of tubular body 52, and second stopper member 66B abuts second end 58 of tubular body 52. Stopper members 66, however, allow tubular body 52 and fins 54 to rotate about guide wire 62. As described in more detail below, the ability of the fins to rotate about guide wire 62 allows positioning device 50 and, in particular, fins 54 to align with the openings between the valve leaflets of a heart valve.

In some example configurations, positioning device 50 may include tip 68 engaged to the distal end of guide wire 62 to aid in advancement of positioning device 50 through a tortuous anatomy en route to the site of the occlusion, e.g., a heart valve. Tip 68 is desirably made from a soft material, such as Pebax 40D, Pebax 55D, or silicone and may be attached to guide wire 62 using any suitable process, such as gluing, heat bonding, RF welding or laser welding. In one example (not depicted), tip 68 may include a radiopaque marker, MRI marker, and the like to help locate positioning device 50 as it is advanced through the body.

As seen in FIG. 3, positioning device 50 includes three fins, namely fins 54A, 54B, and 54C. As described in more detail below, fins 54A, 54B, and 54C can be inserted through a tricuspid heart valve, e.g., aortic valve. In other example configurations, positioning device 50 may include more or fewer fins. For example, positioning device 50 may include two fins for use in a patient that has an occlusion at a base of a bicuspid valve.

In some example configurations, positioning device 50 may include markers to help a clinician visualize the orientation of fins 54 in the body of the patient. For example, positioning device 50 may include radiopaque markers, e.g., gold dots, stripes, and the like, that designate fins 54. In FIG. 3, each fin 54 has a distinctive pattern. For example, fin 54A has a pattern of three dots, shown at 55A. Fin 54B has a pattern of three stripes, shown at 55B. Fin 54C has a pattern of one long stripe, shown at 55C. Of course, numerous other patterns may be used. In the example shown in FIG. 3, the patterns are repeated on each fin 54. In other examples, the patterns may not be repeated, or the patterns may be repeated more often.

In other examples, it may be desirable to include four or more fins on positioning device 50. For example, positioning device 50 may be used to remove calcifications within a body lumen that are not located on a valve. In such an example, positioning device 50 may be used to create sections adjacent the calcification(s) to allow accurately placement of an atherectomy device.

FIG. 4 is an end cross-sectional view of the example positioning device of FIG. 3 taken along line 4-4. In the example shown in FIG. 4, adjacent fins 54, e.g., fins 54A and 54B, are separated by an angle θ of about 120 degrees. In some examples, the angles θ between adjacent fins need not be equal to one another, or equal to 120 degrees.

As mentioned above, positioning device 50 and, in particular, fins 54 divide a body lumen of a patient, e.g., a vessel or artery, into multiple sections. The sections defined by the fins of positioning device 50 and the interior surface of the vessel or artery allow a clinician to accurately locate the atherectomy device against an occlusion, e.g., a calcification, at the base of a heart valve.

FIG. 5 is an end view of the positioning device shown in FIG. 4 positioned adjacent an occlusion within a body lumen, in accordance with this disclosure. FIG. 5 depicts three sections created within body lumen 70, e.g., aorta, by positioning device 50. In particular, FIG. 5 depicts sections 72A, 72B, and 72C (collectively referred to herein as "section 72"). Section 72A is defined by interior surface 74 of lumen 70 and fins 54A, 54C. Section 72B is defined by interior surface 74 and fins 54B, 54B. Section 72C is defined by interior surface 74 and fins 54A, 54C. As a clinician advances an atherectomy device through the body lumen toward an occlusion, e.g., occlusion 76, fins 54 of positioning device 50 guide the atherectomy device directly towards the occlusion, as shown and described in more detail below with respect to FIGS. 6, 11, and 12. For example, in FIG. 5, interior surface 74, fin 54A, and fin 54C constrain an atherectomy device advanced within section 72A such that the atherectomy device is forced against occlusion 76.

Figures 6, 7, 8:
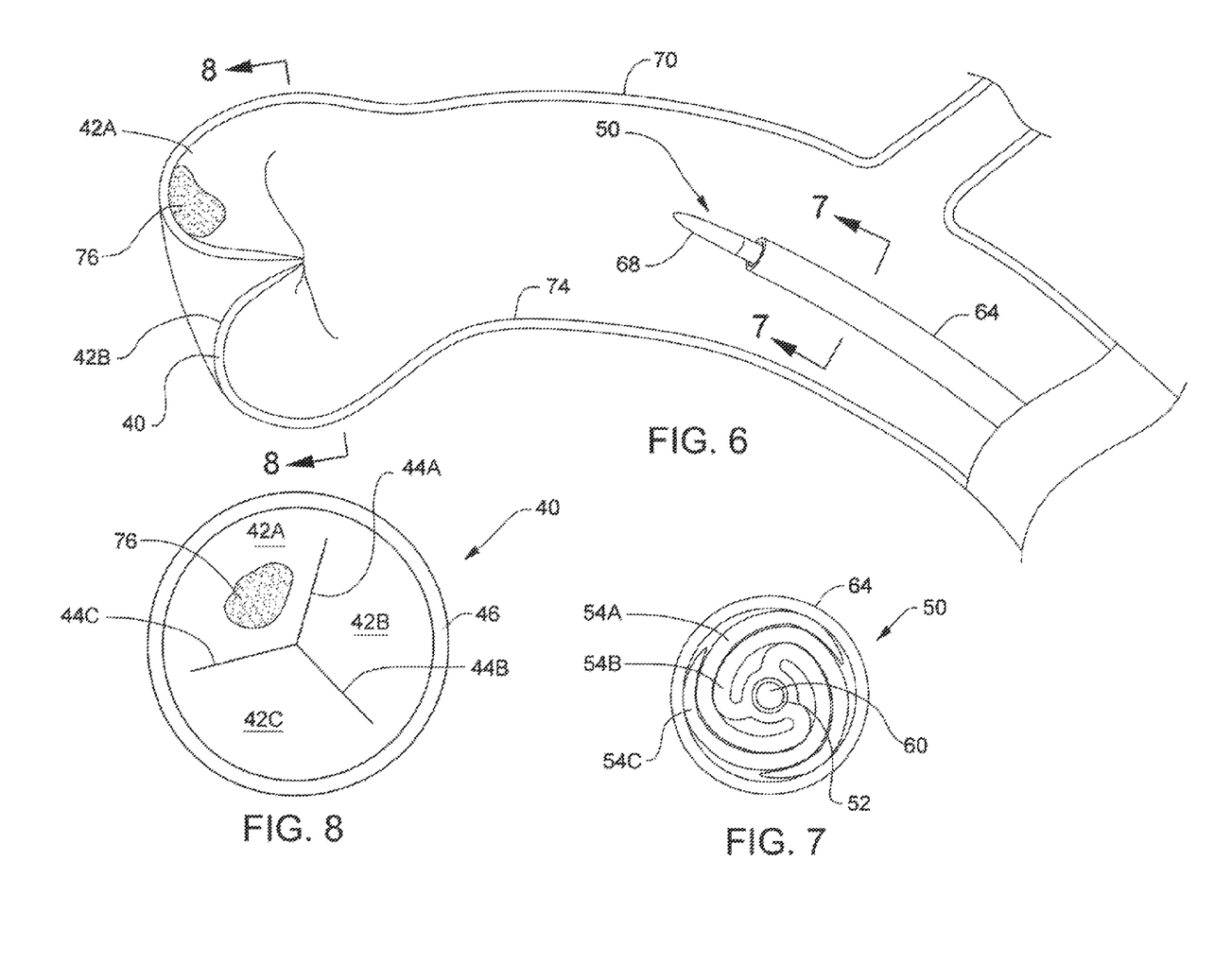
FIG. 6 is a side view of the example positioning device of FIG. 3 in a wrapped state within a body lumen, in accordance with this disclosure.
FIG. 7 is an end cross-sectional view of the example positioning device of FIG. 6, in accordance with this disclosure.
FIG. 8 is an end view of the occluded heart valve depicted in FIG. 6.

FIG. 6 is a side view of the example positioning device of FIG. 3 in a wrapped state within a body lumen, in accordance with this disclosure. More particularly, FIG. 6 depicts a positioning device, constrained by guide catheter 64, being advanced through body lumen 70 by a practitioner toward valve 40, e.g., aortic valve.

As seen in more detail in FIG. 7, when positioning device 50 is in an undeployed or wrapped state, fins 54A, 54B, and 54C wrap around tubular body 52 in one direction and are positioned within a lumen defined by the interior surface of guide catheter 64. As described in more detail below, positioning device 50, in the undeployed state, is advanced through body lumen 70, e.g., the aorta, and through heart valve 40, e.g., aortic valve, and into a chamber of the heart, e.g., left ventricle, prior to removal of guide catheter 64.

FIG. 7 is an end cross-sectional view of the example positioning device shown in FIG. 6 and taken along line 6-6. In the undeployed or wrapped state, fins 54A, 54B, and 54C of positioning device 50 are wrapped around tubular body 52 and are positioned within a lumen defined by the interior surface of guide catheter 64. FIG. 8 is an end view of the occluded heart valve depicted in FIG. 6 and taken along line 7-7.

As indicated above, the techniques described in this disclosure allow an occlusion in one section created by positioning device 50, e.g., section 72A of FIG. 5, to be treated by the atherectomy device while the inlet to the carotid artery is positioned in another section, e.g., section 72C of FIG. 5. In this manner, positioning device 50 may help to prevent debris created by the atherectomy device from being flushed through the carotid artery towards the brain.

Figure 9:
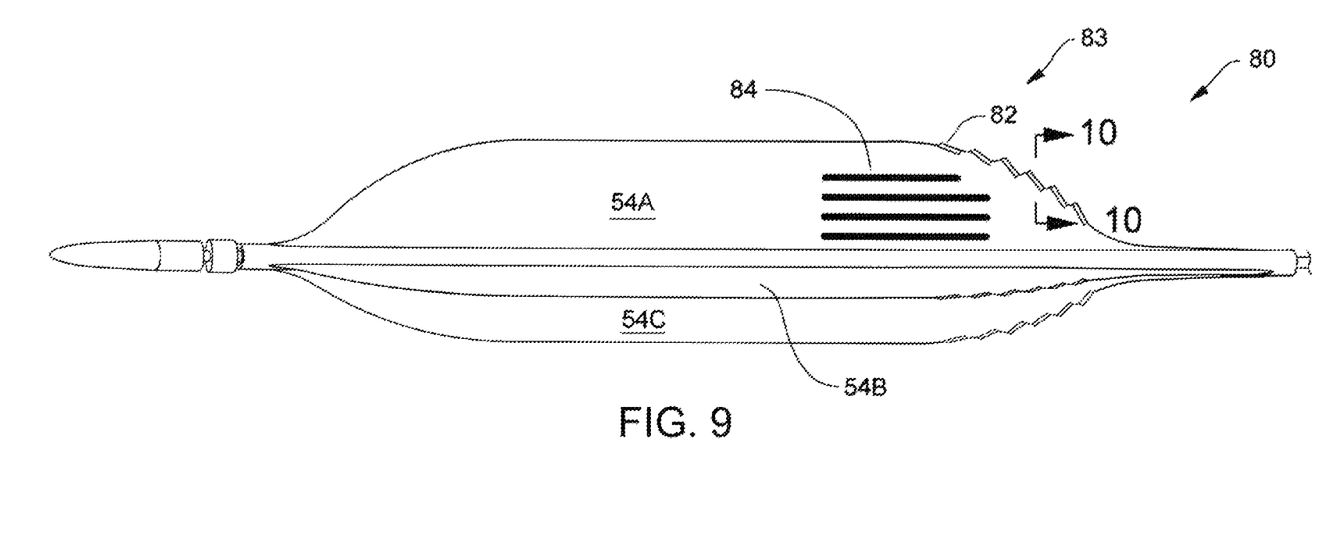
FIG. 9 is a side view of another example of a positioning device that includes a blade, in accordance with this disclosure.

FIG. 9 is a side view of another example of a positioning device that may be used to remove an occlusion, e.g., calcification, within a patient. The positioning device of FIG. 9, shown generally at 80, is similar to positioning device 50 of FIG. 3. In addition to the features described above with respect to FIG. 3, device 80 of FIG. 9 includes one or more blades 82 engaged to a proximal portion of one or more fins 54 to allow positioning device 50 to cut through occlusions, e.g., calcifications, that bridge valve leaflets. For example, positioning device 80 with blade(s) 82 may be used to cut through an occlusion that bridges leaflets 42A and 42C of FIG. 2.

Figure 10:
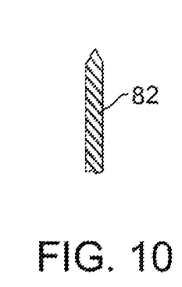
FIG. 10 is an end view of the blade in the example positioning device of FIG. 9.

The example positioning device 80 of FIG. 9 includes three blades, namely 82A, 82B, and 82C, respectively engaged to a proximal portion of fins 54A, 54B, and 54C, shown generally at 83. Blades 82 may be constructed of multiple separate smaller blades, where each smaller blade jumps backward from the smaller blade in front. Numerous other blade constructions are possible and are considered within the scope of this disclosure. FIG. 10 is an end view of one example blade shown in FIG. 9. As seen in FIG. 10, blade 82, which includes multiple smaller blades, presents a jagged edge for cutting through occlusions, e.g., calcifications.

Blades 82 may be made of metal or diamond, for example, to allow positioning device 80 to cut through calcifications that extend between valve leaflets. Other blade materials, however, may be desirable and are considered to be within the scope of this disclosure.

In operation, as a practitioner pulls device 80 proximally through valve 40, fins 54 rotate and self-align with the openings defined by the valve leaflets, e.g., openings 42A, 42B, and 42C of FIG. 2. Continuing to pull positioning device 80 proximally causes the blade(s) 82 to cut through the occlusions, e.g., calcifications, that bridge two valve leaflets and prevent its proper operation. The practitioner may repeat the process by distally advancing positioning device 80 and then pulling device 80 proximally until the occlusive bridge between valve leaflets has been severed.

In some example configurations, one or more fins 54 of positioning device 80 of FIG. 9 (or device 50 of FIG. 3) may alternatively or additionally include an abrasive material disposed along the surface area of a fin, depicted by the lines indicated generally by 84 on fin 54A. As a practitioner advances and retracts device 80 through a valve, e.g., valve 40 of FIG. 2, abrasive material 84 on one or more of fins 54 may act like a rasp to scrap or file down the occlusive material, e.g., calcification. For example, one or more blades 82 may be used to cut through a calcification that bridges two leaflets, then the abrasive material may be used to scrap or file away additional occlusive material to improve valve performance. In other examples, fins 54 may comprise abrasive material only, without a blade. For example, device 50 of FIG. 3 may include abrasive material 84 of FIG. 9.

Using the positioning device described above, a clinician may guide an atherectomy device, e.g., as shown and described below with respect to FIG. 1, into one of the sections created by the positioning device toward a calcified area, e.g., at the base of a heart valve. Example deployment and operation of the positioning device will be described below with respect to FIGS. 6 and 12-14.

As seen in FIG. 6, positioning device 50 is advanced through body lumen 70, e.g., the aorta, in a wrapped (or undeployed) state toward an occlusion. In particular, in the wrapped state shown in FIG. 6, positioning device 50 is advanced along guide wire 62 (shown in FIG. 3) through body lumen 70 with fins 54 wrapped around tubular body 52 and covered by guide catheter 64. In the example depicted in FIG. 6, positioning device 50 is advanced toward occlusion 76 located at heart valve 40, e.g., aortic valve.

Figure 11:
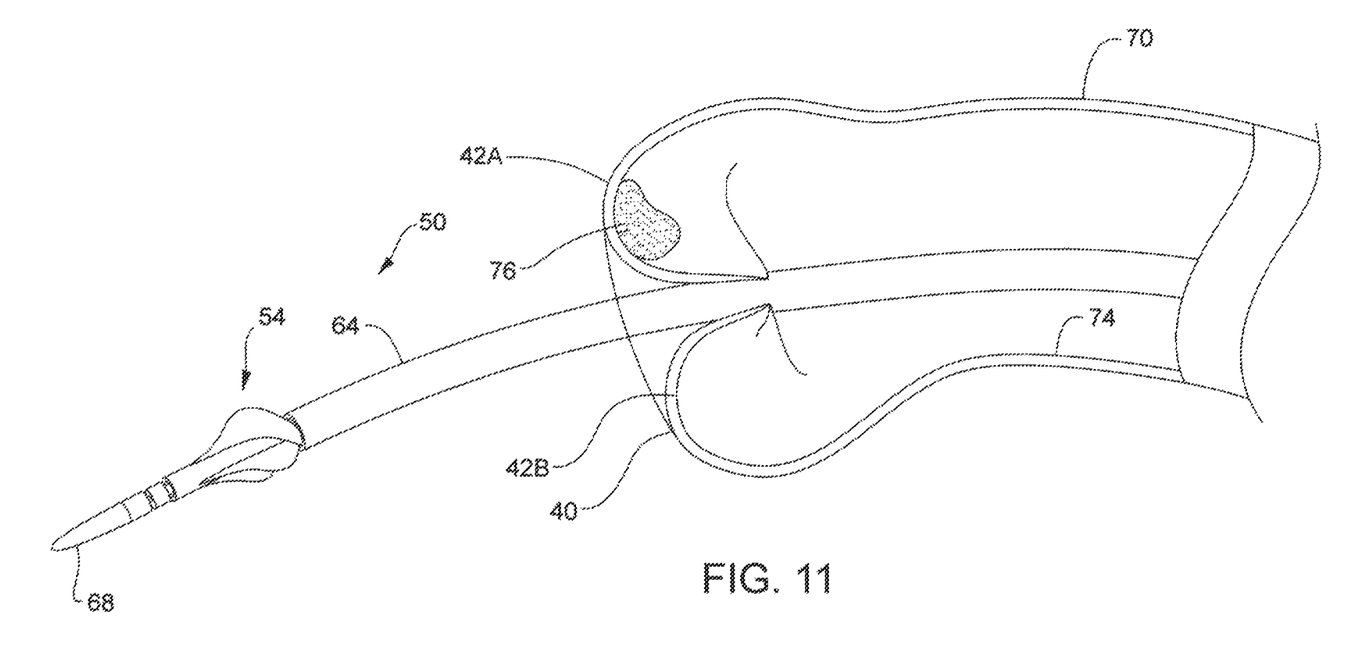
FIG. 11 is a side view of the example positioning device of FIG. 3 in a partially unwrapped state within a heart chamber, in accordance with this disclosure.

FIG. 11 is a side view of the example positioning device of FIG. 3 in a partially unwrapped state within a heart chamber, in accordance with this disclosure. In particular, FIG. 11 depicts positioning device 50 of FIG. 6 advanced through body lumen 70, e.g., the aorta, and through heart valve 40, e.g., aortic valve, and into a chamber of the heart, e.g., left ventricle, prior to removal of guide catheter 64. As seen in FIG. 11, once the practitioner has advanced positioning device 50 through heart valve 40, the practitioner begins to pull guide catheter 64 proximally, thereby causing the fins, shown generally at 54, to unfold from their wrapped state and return to their original, deployed shape without assistance.

FIG. 12 is a side view of the example positioning device of FIG. 3 in an unwrapped state extending through an occluded heart valve, in accordance with this disclosure. More particularly, once the practitioner has completely retracted guide catheter 64 from positioning device 50 of FIG. 11, which allows fins 54 to completely unfold into the position shown in FIG. 12, for example, the practitioner pulls device 50 proximally. Pulling device 50 proximally causes fins 54 to rotate and self-align with the openings defined by the valve leaflets. Stoppers 66A and 66B prevent tubular body 52 and fins 54 from moving longitudinally along the length of guide wire Continuing to pull device 50 proximally causes positioning device 50 to extend through the openings defined by the valve leaflets. As seen in FIG. 12, positioning device 50 is positioned adjacent the occlusion, e.g., occlusion 76 of FIG. 12, and positioned such that a distal portion of device 50 is located in one chamber of the heart, e.g., left ventricle, and a proximal portion is located in a body lumen, e.g., aorta. Valve 40 in FIG. 12 and, more particularly, valve leaflets 42 are able to open and close with positioning device 50 extending through valve 40, with blood flow is minimally obstructed.

FIG. 12 further depicts an atherectomy device, e.g., a Rotablator® or atherectomy device of FIG. 1, being advanced by a practitioner toward occlusion 76 located at the basal area of valve 40, after guide catheter 86 has been refracted. In particular, and in accordance with various techniques of this disclosure, the practitioner advances the atherectomy device toward occlusion 76 via a section, e.g., section 72A of FIG. 13, defined by the fins 54A and 54C of positioning device 50 and interior wall 74 of body lumen 70. As indicated above, positioning device 50 and, in particular, fins 54 divide a body lumen of a patient, e.g., a vessel or artery, into multiple sections. The sections created by the positioning device help focus the atherectomy device toward the occlusion and aid the practitioner in accurately positioning the atherectomy device. In this manner, occlusions that would otherwise be difficult to treat, e.g., at a valve, can be ablated. In some examples, the atherectomy device may further include filter 88 to capture the occluded material dislodged during the atherectomy procedure.

If two or more occlusions at a valve exists, e.g., valve 40 of FIG. 12, the practitioner may pull the atherectomy device proximally out of a first section defined by the positioning device after having finished ablating a first occlusion at a first location. Then, the practitioner may guide the atherectomy device into a second section defined by the positioning device in order to begin ablating a second occlusion at a second location.

FIG. 13 is an end view of the occluded heart valve and positioning device shown in FIG. 12 and taken along line 13-13, in accordance with this disclosure. In FIG. 13, movement of valve leaflets 42 is indicated by lines 90 while positioning device 50 extends through the valve.

Figure 14:
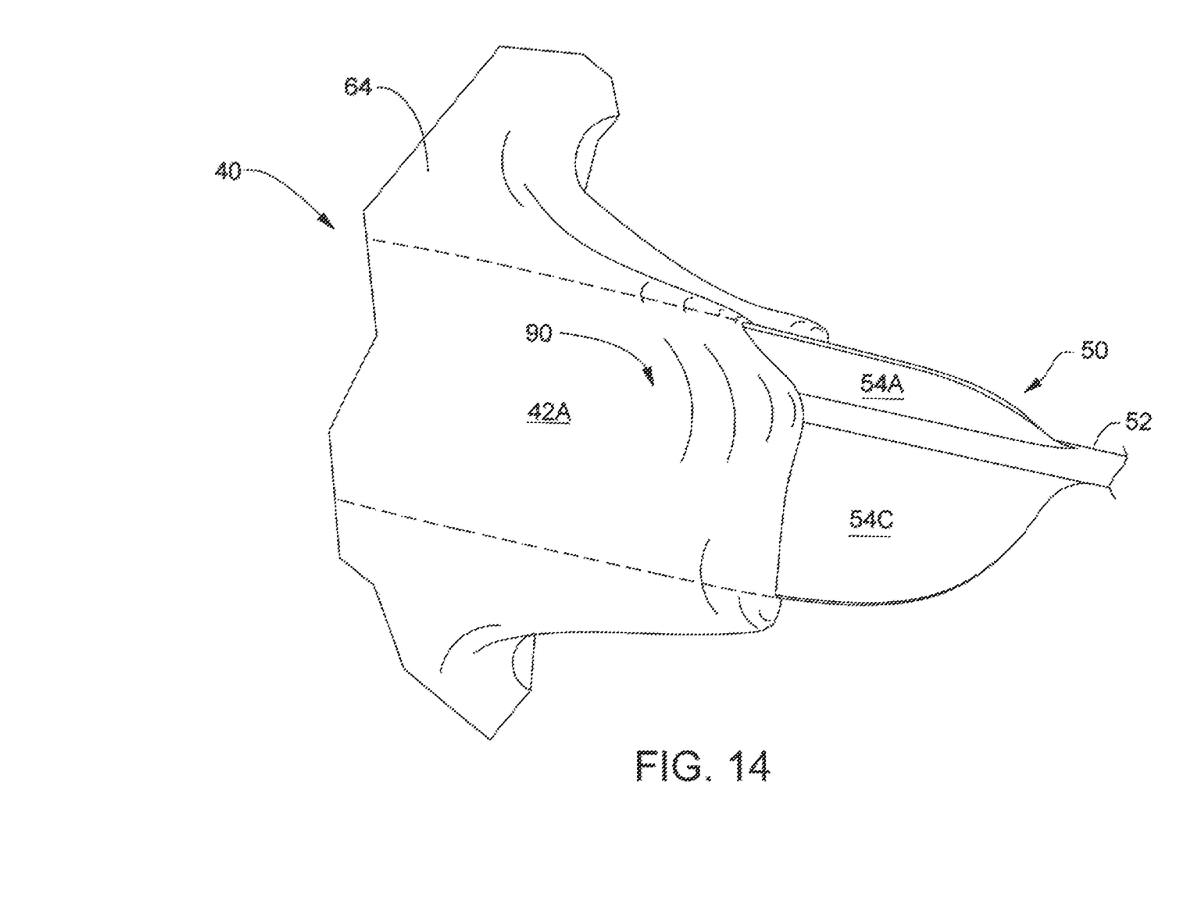
FIG. 14 is a perspective view of a portion of a heart valve and the positioning device, in accordance with this disclosure.

FIG. 14 is a perspective view of a portion of a heart valve and the positioning device, in accordance with this disclosure. In particular, FIG. 14 depicts a portion of positioning device 50 of FIG. 12 extending through a portion of valve 40 of FIG. 12. As indicated by lines 90 in FIG. 14, valve leaflets, e.g., leaflets 42A, are able to open and close against fins 54 of positioning device 50, e.g., fins 54A and 54C, which allows valve 40 to continue to function during the atherectomy procedure.

Figure 15:
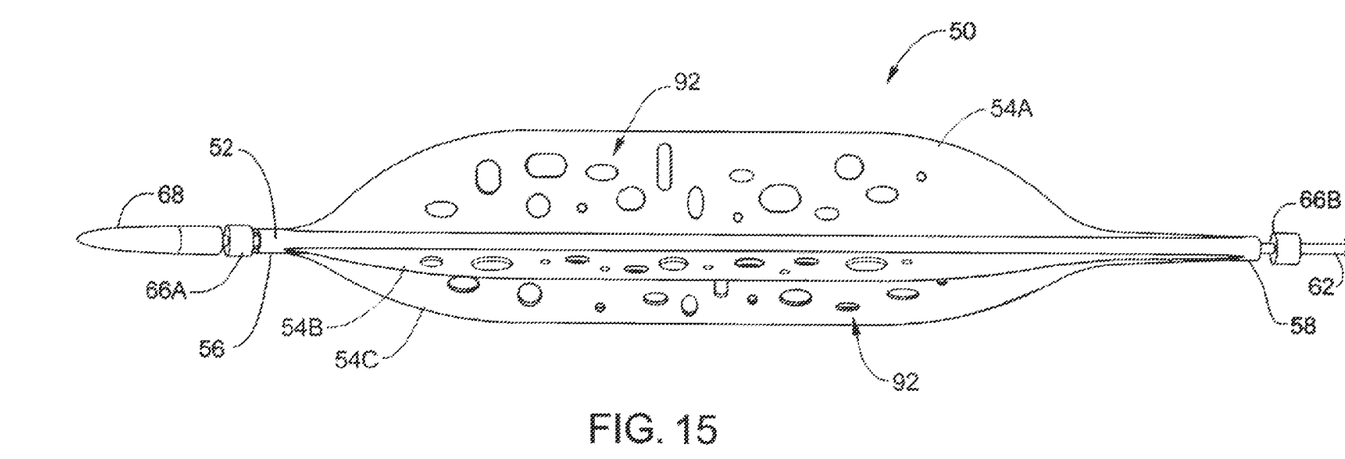
FIG. 15 is a side view of another example of a positioning device in an unwrapped state, in accordance with this disclosure.

FIG. 15 is a side view of another example of a positioning device in an unwrapped state, in accordance with this disclosure. In particular, FIG. 15 depicts an example positioning device 50 where each of fins 54 define a plurality of holes, shown generally at 92. During some atherectomy procedures, it may be difficult to place the atherectomy device because of fluctuating and fast moving blood stream. Instead of having closed fins that allow no blood flow between adjacent sections (as in FIG. 3), the example positioning device 50 in FIG. 15 includes holes 50 that allow blood to pass through fins 54. Holes 50 allow the atherectomy device to guided while blood flows between adjacent sections 72. Holes 50 may be various shapes and sizes, as desired. Holes 50 may be small enough to prevent debris from flowing between sections. In this manner, holes 50 may be sized to act like filters.

Figure 16:
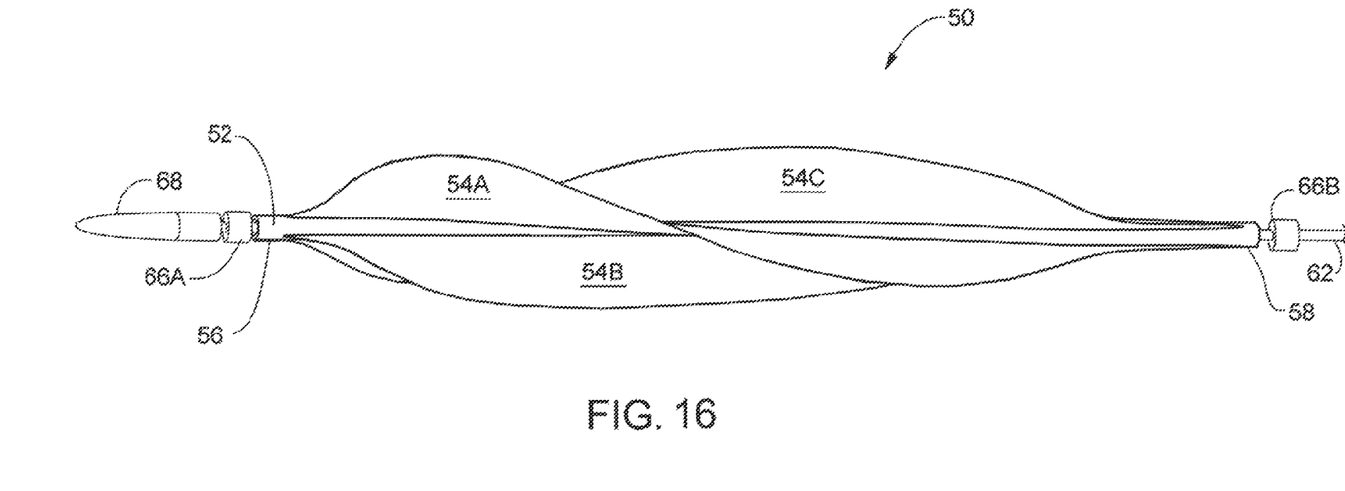
FIG. 16 is a side view of another example of a positioning device in an unwrapped state, in accordance with this disclosure.

FIG. 16 is a side view of another example of a positioning device in an unwrapped state, in accordance with this disclosure. As indicated above, the techniques described in this disclosure allow an occlusion in one section created by the positioning device to be treated by the atherectomy device while the inlet to the carotid artery is positioned in another section. FIG. 16 depicts positioning device 94 having a twisted fin configuration that may be used to treat a section with an occlusion, e.g., section 72A of FIG. 5, that are in the same angular orientation as the carotid artery inlet, for example. In this manner, the twisted fin configuration of positioning device 94 routes debris away from the carotid artery even though the occlusion being treated is in the same angular orientation as the carotid artery inlet.

Figure 17:
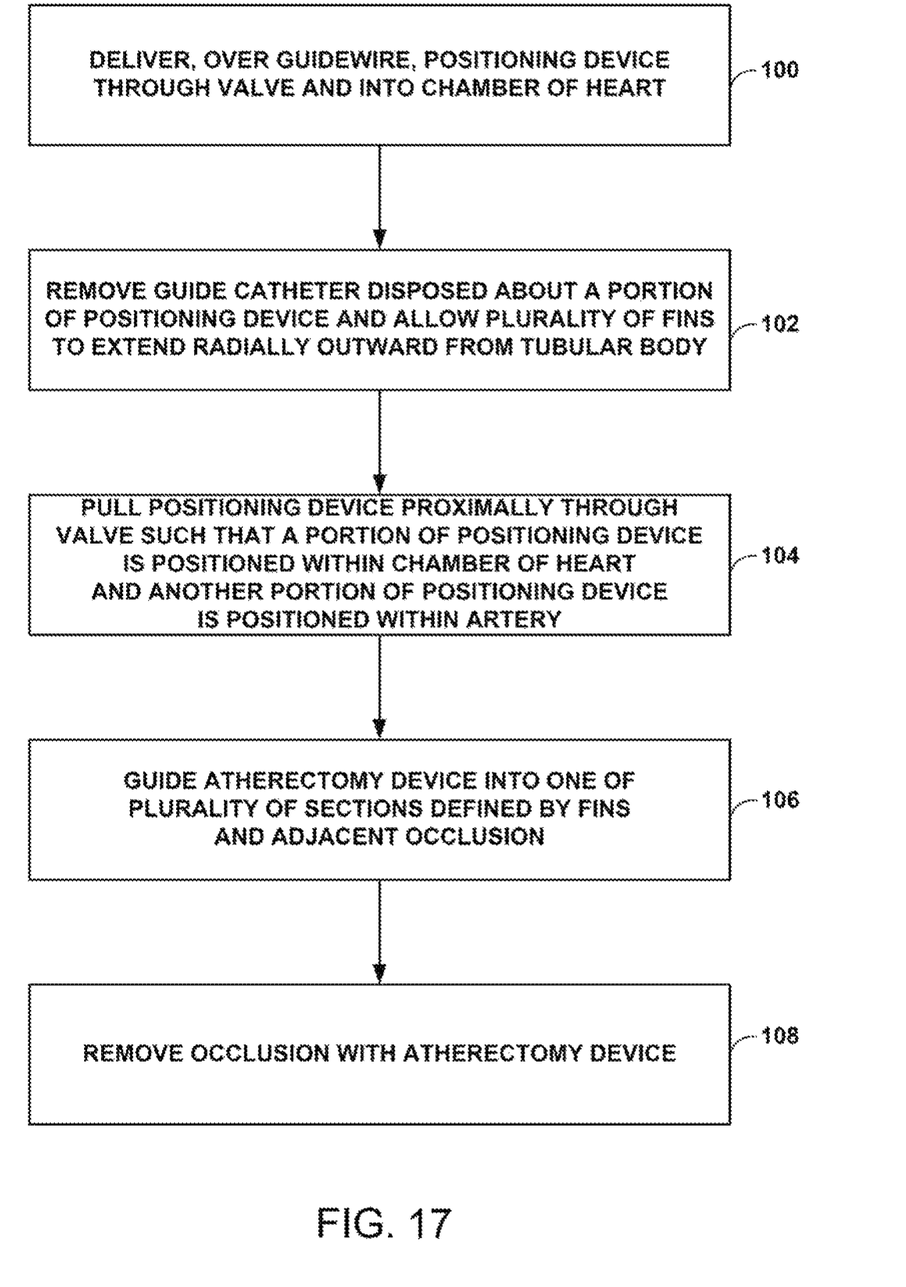
FIG. 17 is a flow diagram illustrating an example method for removing an occlusion using a positioning device, in accordance with this disclosure.

FIG. 17 is a flow diagram illustrating an example method for removing an occlusion using a positioning device, in accordance with this disclosure. A practitioner, e.g., clinician, delivers, over a guide wire, e.g., guide wire 62, a positioning device, e.g., positioning device 50 or positioning device 80, into a chamber of a heart, e.g., left ventricle (100). In other example implementations, the practitioner may insert the guide wire 62 into a body lumen for removal of an occlusion within the body lumen itself After the positioning device has been delivered, the practitioner pulls proximally a guide catheter, e.g., guide catheter 64, disposed about at least a portion of the positioning device, which allows a plurality of fins, e.g., fins 54A-54C, to unwrap from tubular body 52 and extend radially outward from tubular body 52 (102).

Once fins 54 have unwrapped from around tubular body 52 of the positioning device, the practitioner pulls positioning device 50 proximally through valve 40 such that a portion of positioning device 50 is positioned within the chamber of the heart and another portion of the positioning device is positioned within an artery, e.g., aorta, whereby extended fins 54 define a plurality of sections 72 within the artery (104). While the practitioner is pulling the positioning device, fins 54 rotate and self-align to match the openings 44 between valve leaflets 42. While the positioning device extends through valve 40, valve leaflets 42 continue to open and close, thereby maintaining the functionality of valve 40.

The practitioner guides an atherectomy device (e.g., a Rotablator® atherectomy device, athrectomy device 10 of FIG. 1, and the like) into one of the plurality of sections 72 defined by fins 54 of positioning device 50 (106). The practitioner then further advances the atherectomy device adjacent to an occlusion, e.g., occlusion 76 of FIG. 12, within the patient, and removes the occlusion with the atherectomy device (108).

In example configurations that include a blade, e.g., positioning device 80 of FIG. 9, the method may further include the act of cutting, via the blade, a material extending between two leaflets of the valve.

If a second occlusion (or more) is present on the valve, the method shown in FIG. 15 may further include the acts of pulling the atherectomy device proximally away from the positioning device, guiding the atherectomy device into another one of the plurality of sections defined by the fins and adjacent a second occlusion, and removing the second occlusion.

Various aspects of the disclosure have been described. These and other aspects are within the scope of the following claims.

The invention claimed is:

1. A system for treating an occlusion in a patient, the system comprising:
an atherectomy device configured to remove an occlusion from a body lumen; and
a positioning device that positions the atherectomy device adjacent to the occlusion, the positioning device comprising:
a tubular body having a first end and a second end and defining a lumen therebetween;
at least two fins engaged to the tubular body, the fins configured to move between a deployed state, in which the at least two fins extend radially outward from the tubular body, and an undeployed state, in which the at least two fins are folded to wrap around one another and around the tubular body;
a guide wire extending through the lumen; and
first and second stopper members, each of the first and second stopper members engaged to the guide wire, wherein the first stopper member and the second stopper member substantially prevent movement of the tubular body along the guide wire.

2. The system of claim 1, the positioning device further comprising a blade, wherein the blade is engaged to a proximal portion of one of the fins.

3. The system of claim 1, wherein the tubular body is configured to rotate around the guide wire.

4. The system of claim 1, wherein the at least two fins comprise three fins.

5. The system of claim 4, wherein, in the deployed state, an angle of about 120 degrees separates adjacent fins.

6. The system of claim 5, wherein, in the deployed state, the three fins are configured to extend through an opening of a tricuspid valve.

7. The system of claim 1, wherein the first stopper member and the second stopper member comprise a first ring and a second ring, respectively.

8. The system of claim 1, wherein the first stopper member abuts a first end of the tubular body, and wherein the second stopper member abuts a second end of the tubular body.

9. A positioning device that positions an atherectomy device adjacent to an occlusion in a patient, the positioning device comprising:
a tubular body having a first end and a second end and defining a lumen therebetween;
at least two fins engaged to the tubular body, the fins configured to move between a deployed state, in which the at least two fins extend radially outward from the tubular body, and an undeployed state, in which the at least two fins are folded to wrap around one another and around the tubular body;
a guide wire extending through the lumen; and
first and second stopper members, each of the first and second stopper members engaged to the guide wire, wherein the first stopper member and the second stopper member substantially prevent movement of the at least two fins along the guide wire.

10. The positioning device of claim 9, further comprising a blade, wherein the blade is engaged to a proximal portion of one of the fins.

11. The positioning device of claim 9, wherein the tubular body is configured to rotate around the guide wire.

12. The positioning device of claim 9, wherein the at least two fins comprise three fins.

13. The positioning device of claim 12, wherein, in the deployed state, an angle of about 120 degrees separates adjacent fins.

14. The positioning device of claim 12, wherein, in the deployed state, the three fins are configured to extend through an opening of a tricuspid valve.

15. The positioning device of claim 9, wherein the first stopper member and the second stopper member comprise a first ring and a second ring, respectively.

16. The positioning device of claim 9, wherein the first stopper member abuts a first end of the tubular body, and wherein the second stopper member abuts a second end of the tubular body.

* * * * *